Figure 1:
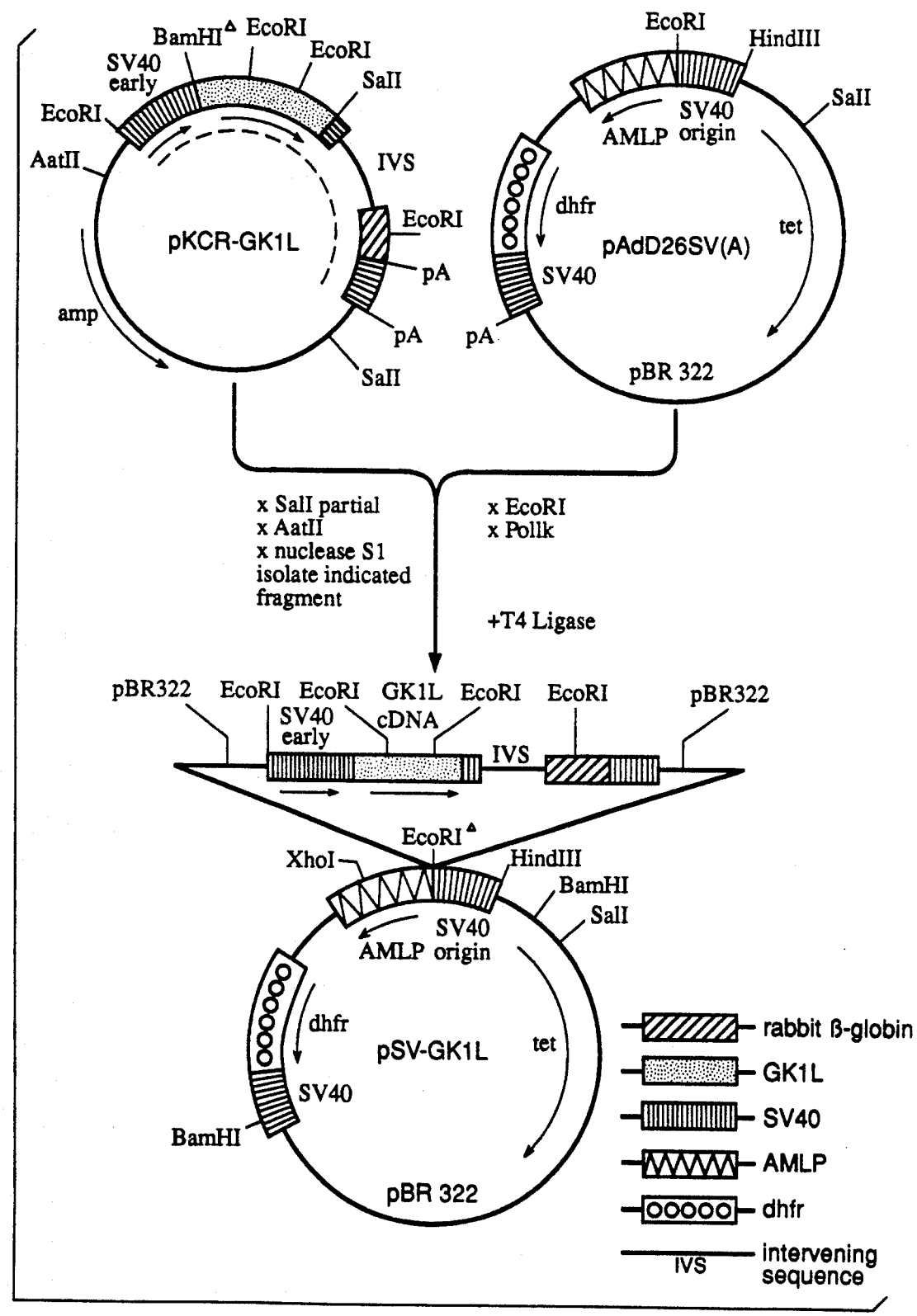

United States Patent [19]

Weidle et al.

[11] Patent Number: 5,223,422
[45] Date of Patent: Jun. 29, 1993

[54] T-PA MUTANT GK1L

[75] Inventors: Ulrich Weidle, München; Anne Stern, Penzberg, both of Fed. Rep. of Germany

[73] Assignee: Boehringer Mannheim GmbH, Mannheim, Fed. Rep. of Germany

[21] Appl. No.: 671,776

[22] PCT Filed: Aug. 22, 1990

[86] PCT No.: PCT/EP90/01401
§ 371 Date: May 24, 1991
§ 102(e) Date: May 24, 1991

[87] PCT Pub. No.: WO91/02798
PCT Pub. Date: Mar. 7, 1991

[30] Foreign Application Priority Data

Aug. 23, 1989 [DE] Fed. Rep. of Germany ....... 3927865

[51] Int. Cl.⁵ .................. A61K 37/48; C12N 9/50; C12N 9/64; C12N 15/58
[52] U.S. Cl. ............................. 435/212; 435/226; 435/69.6; 435/240.2
[58] Field of Search ............ 435/215, 212, 226, 172.3, 435/216; 424/94.63, 94.64

[56] References Cited
FOREIGN PATENT DOCUMENTS
WO8703906 7/1989 PCT Int'l Appl.

OTHER PUBLICATIONS
Kagitani et al., FEBS. 189(1): 145–149 (1985).
Stern et al., Gene 79: 333–344 (1989).
Stern et al., Gene 87: 305–308 (1990).

Primary Examiner—Robert A. Wax
Assistant Examiner—Dian Jacobson
Attorney, Agent, or Firm—Felfe & Lynch

[57] ABSTRACT

The invention concerns a recombinant DNA which codes for a protein with the domains G, K1 and L of t-PA in which the sequences coding for the domains K2 and F of the wild-type t-PA gene or the sequences derived therefrom within the scope of the degeneration of the genetic code are completely deleted according to the exact exon/intron borders on the t-PA gene. The invention also relates to a process for the production of a recombinant DNA according to the present invention. In addition the invention concerns vectors containing this recombinant DNA as well as cells which are transformed with vectors according to the present invention or with the DNA according to the present invention. Furthermore the invention provides a protein with fibrinolytic properties by expression of a DNA sequence according to the present invention in suitable host cells which consists of the amino acid sequences of the domains G, K1 and L of t-PA in this order and which, if desired, is glycosylated as well as a process for its production. Finally the invention also concerns a fibrinolytic agent containing a protein according to the present invention.

3 Claims, 3 Drawing Sheets

T-PA MUTANT GK1L

Human tissue plasminogen activator (t-PA) is a serine protease with a molecular weight of 68000 daltons which converts the pro-enzyme plasminogen into the active serine protease plasmin. Plasmin dissolves fibrin which is the main component of the protein matrix of coagulated blood. t-PA has a high affinity for fibrin and is also activated by fibrin (see Fibrinolysis 2 (1988), 133–142). t-PA is therefore of great medical interest.

An advantage of t-PA compared to other known plasminogen activators, such as e.g. urokinase or streptokinase, is the ability to stimulate its catalytic activity by fibrin (see J. Biol. Chem. 257 (1982), 2912–2919; Biochem. Biophys. Acta 755 (1983) 531–533).

t-PA (amino acid sequence cf. Vehar et al., Bio/-Technology 2 (1984) 1051–1057) in its single-chain form consists of a heavy chain (H chain) and a light chain (L chain) which are held together by a disulphide bridge. The two-chain form is formed from a single-chain precursor form by specific cleavage with plasmin or other proteases between the amino acids (aa) 275 and 276. The heavy L chain of 32000 daltons weight contains the enzymatically active region which has homologies to other serine proteases such as urokinase or plasmin (Proc. Natl. Acad. Sci. USA 81 (1984), 5335–5339). The domains on the H chain of 39000 daltons weight are the finger domain (F) with homology to fibronectin (aa 1–49), the growth factor domain (G) with homology to mouse and human epidermal growth factor (aa 50–87) and two kringle domains, K1 (aa 88–175) and K2 (aa 176–262) with homology to the kringle structures in plasminogen.

Concerning the function of the individual domains of the H chain it is already known that only the domains K2 or/and F but not the domain K1 are responsible for binding of t-PA to fibrin and thus for the ability to stimulate the catalytic activity of t-PA in the presence of fibrin (EP-A-0 234 051).

It is known from EMBO 7 (1988) 2731–2740 that the activity of a t-PA mutant containing the complete domains K1 and F as well as a part of domain K2 of the H chain can also be stimulated by fibrin.

It is thus not clear to what extent the individual domains of the H chain effect the activity of the t-PA molecule with regard to fibrin and to what extent they cause a stimulation of the plasminogen cleaving activity.

The object of the present invention is to provide a t-PA mutant which has greater plasminogen cleaving activity than t-PA and whose catalytic activity can also be stimulated by fibrin or fibrinogen.

This object is achieved according to the present invention by the production of a recombinant DNA which codes for a protein with the domains GK1L of t-PA whereby the sequences coding for the domains K2 and F or sequences derived therefrom within the scope of the degeneration of the genetic code are completely deleted i.e. according to the exact exon/intron borders on the t-PA gene. The nucleotides 715 to 972 and 199 to 339 of the t-PA cDNA are therefore missing from the recombinant DNA according to the present invention (numbering according to Nature 301, (1983), 214–221). Surprisingly the ability to stimulate the catalytic activity by fibrin is preserved in GK1L although in the t-PA mutant GK1L the domains K2 and F of the H chain which are regarded as absolutely essential for stimulating the activity are completely missing from the gene product of the recombinant DNA according to the present invention. Surprisingly the catalytic activity of a supernatant from cells which express GK1L is even significantly higher than the activity of a supernatant from cells which express t-PA.

The invention also provides a process for the production of recombinant DNA according to the present invention from a DNA sequence coding for t-PA or for a t-PA mutant which contains more than the domains G, K1 and L by deletion of those sequences which do not code for the domains G, K1 and L while maintaining the exact exon/intron borders on the t-PA gene. A process is particularly preferred in which the deletion of the DNA coding for the domains K2 and F is carried out by site-directed mutagenesis.

The invention also provides a recombinant vector which contains one or several copies of the recombinant DNA according to the present invention. In this connection a preferred embodiment is a vector which is suitable for the expression of the recombinant DNA in eukaryotic cells. A particularly preferred embodiment of the invention is a eukaryotic vector with the GK1L gene which contains the early SV40 promoter and a mouse dhfr⁻ gene. However, the plasmid pSV-GK1L according to the present invention is most preferred.

Furthermore the invention provides a cell line which is transformed with the recombinant DNA according to the present invention or a vector according to the present invention. Particularly preferred is a eukaryotic cell line, most preferred being a CHO dhfr⁻ cell line (e.g. ECACC 88072103), which contains a recombinant DNA according to the present invention or a vector according to the present invention.

The invention also provides a protein with fibrinolytic properties which consists of the amino acid sequences of the domains G, K1 and L of t-PA in this order and which is glycosylated, if desired. The invention also includes a process for the production of a protein with fibrinolytic properties in which a recombinant DNA according to the present invention or a vector according to the present invention is expressed in suitable host cells and the expression product is obtained from the culture medium or by lysis of the host cells. In this connection a process is preferred in which the protein according to the present invention is obtained from eukaryotic host cells, preferably CHO dhfr⁻ cells, in a glycosylated form. Surprisingly a supernatant from CHO dhfr⁻ cells, which are transformed with the plasmid pSV-GK1L according to the present invention and which secrete GK1L, has a higher catalytic activity than the supernatant from cells which are transformed with a corresponding expression vector pSV-FGK1K2L on which the wild-type t-PA gene is present.

A process is particularly preferred in which host cells are used which are cultured in a medium containing aprotinin.

Surprisingly in this case the activity as well as the extent of stimulation by fibrin is higher in the supernatant of host cells when the culture medium contains aprotinin.

Finally the invention provides a fibrinolytic agent which contains a protein according to the present invention.

Figure 2:
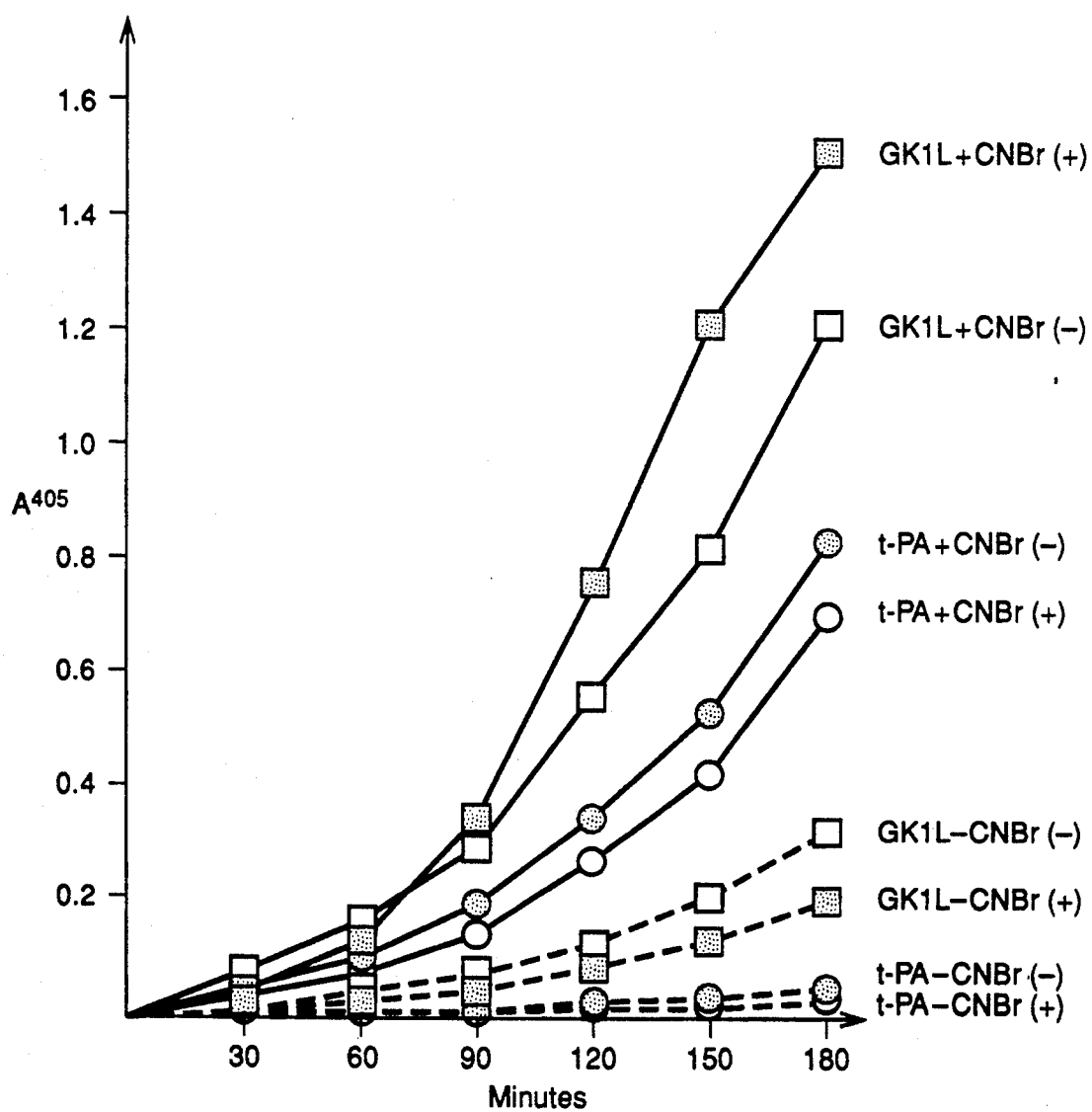

The following Examples in conjunction with the FIGS. 1 and 2 are intended to elucidate the invention further.

They show:

FIG. 1 the production of plasmid pSV-GK1L,

FIG. 2 a comparison of the fibrinogen-stimulated catalytic activity of wild-type t-PA and GK1L.

Figure 3:
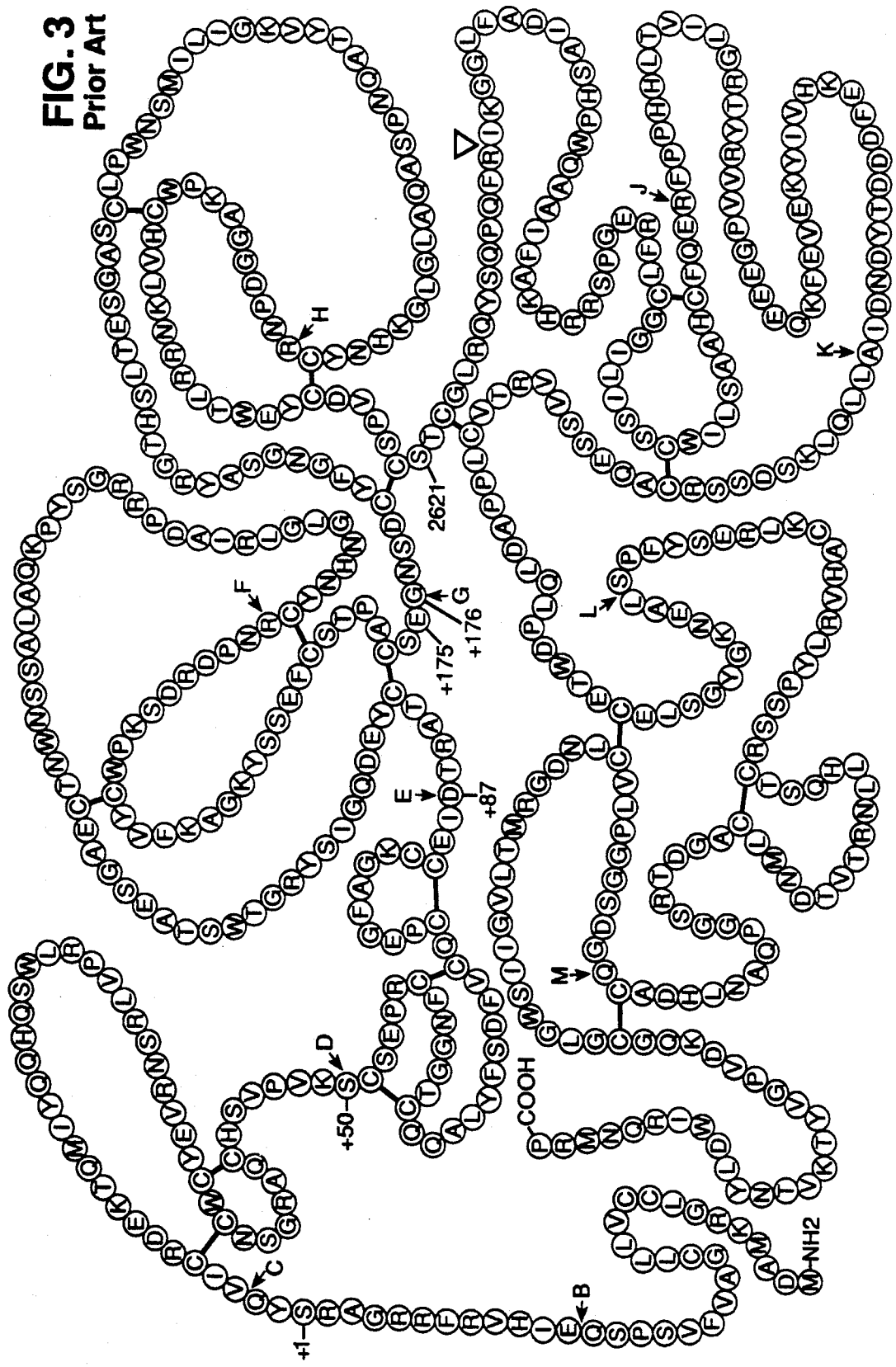

FIG. 3 shows the structure and amino acid sequence of wild-type t-PA molecule.

EXAMPLE 1

Production of a t-PA derivative in which the finger and kringle 2 domains are deleted (GK1L)

The production of the deletion mutant FGK1L from t-PA cDNA was carried out by deletion of the kringle 2 domain by site-directed mutagenesis according to the process from Bio/Technology 2 (1984), 636-639. pePA 133 (produced according to EP-A 0242836) served as the starting plasmid on which the t-PA nucleotide sequence 190-1809 is present. The mutagenesis primer 1 (5' GCCTGCTCTGAGTCCACCTGCGGC 3') was used to remove the nucleotides 715 to 972 (exons VIII and IX) (according to the numbering of t-PA cDNA in Nature 301 (1983), 214-221). A plasmid p7745 which codes for the deletion mutant FGK1L was then isolated by colony hybridization with the mutagenesis primer 1 and sequenced. A reconstitution of the t-PA signal sequence was necessary for the expression later in eukaryotic cells.

At first the FGK1L cDNA was provided with the leader sequence and the 3'UT (3' untranslated region) corresponding to the original cDNA sequence. For this plasmid p7.1, DSM 4719, which contained in the polylinker of pUC12 the 5'UT (5' untranslated region) up to position 77, the leader sequence and the N-terminal sequence of t-PA up to and including nucleotide position 208, is cleaved with Pst I and Hind III (ca. 2.7 kb). In addition fragments containing the following t-PA cDNA sequences were isolated: a Pst I/Hae II fragment from p7745 which comprises nucleotide positions 209 to 421 as well as a Hae II/EcoRI fragment with the nucleotide positions 421 to 1273 in which nucleotide positions 715 to 972 are deleted by mutagenesis and an Eco RI/Hind III fragment with nucleotide positions 1274-2165 from pePA 98.1 (production see EP-A 0 242 836).

The fragments were ligated and transformed in E. coli DSM 3689. Plasmids carrying transformants were selected in the culture medium by addition of 50 μg/ml ampicillin. The correct plasmid, denoted pePA 159, was verified by restriction enzyme analysis. The FGK1L cDNA could be isolated from this plasmid as an XbaI-HindIII fragment (with a signal sequence but without its own polyadenylation site). This fragment contains a 7 nucleotide 5' untranslated region (5' UT) and the 3' untranslated region (3' UT) up to the BglII site at position 2160 (Nature 301 (1983) 214-221). The mutagenesis primer 2 (5' GATCTTACCAATGCAGCGAGC3') was used for the deletion of the finger domain F (exon IV) from FGK1L. The nucleotides 199 to 339 were removed from the t-PA cDNA by site-directed mutagenesis. A plasmid with the recombinant DNA having the domain composition GK1L was isolated by colony hybridization with mutagenesis primer 2 and sequenced. This was carried out as follows: The filters with immobilized DNA were pre-hybridized for 4 hours at 65° C. in 0.2% SDS, 1.0% Sarkosyl ®, 4x SET (0.6 mmol/l NaCl, 0.2 mol/l Tris-HCl, pH 8.0, 4 mmol/l EDTA) and 4x Denhardt's solution (0.08% Ficoll ®, 0.08% polyvinylpyrrolidone, 0.08% bovine serum albumin).

The hybridization was carried out for 12 hours at 46° C. in 0.2% SDS, 1.0% Sarkosyl ®, 4x SET, 4x Denhardt's and with 5×10$^6$ cpm kinased mutagenesis primer per filter. The filters were washed 3×5 minutes at room temperature, afterwards they were washed 1×10 minutes at 37° C. and 1×5 minutes at 50° C. in 4x SET, 0.2% SDS.

EXAMPLE 2

Immunological characterization of GK1L from CHO cells t-PA cDNA and GK1L cDNA were inserted into the single BamHI cleavage site of the plasmid pKCR (Proc. Natl. Acad. Sci. USA 78 (1981), 1527-1531) as XbaI-HindIII fragments from which the plasmids pKCR-FGK1K2L and pKCR-GK1L were formed. For this the ends of the fragments were filled up with the Klenow fragment of polymerase I. Both cDNAs contained seven authentic nucleotides at the 5' end and their own polyadenylation sites were missing. Both plasmids imparted bacteria with resistance against the antibiotic ampicillin (Amp). The expression of both cDNAs is driven by the SV40 early promoter. On the cDNA this is followed in the plasmid by the large intron of rabbit-β-globin and polyadenylation sites of rabbit-β-globin and SV40. In order to isolate this expression cassette pKCR-FGK1K2L and pKCR-GK1L were linearized by partial cleavage with SalI and then cut with AatII and the protruding ends were degraded with nuclease S1. This fragment was isolated from a low-melting agarose gel and ligated into the filled-up single EcoRI cleavage site of pAdD26SV(A) (J. Mol. Biol. 159 (1982) 601-621). pAdD26SV(A) contains an expression cassette for mouse cDNA which is driven by the major late promoter of adenovirus 2 (AMLP), the SV40 origin of replication and it imparts bacteria with resistance against the antibiotic tetracyclin. The orientation of the expression cassette for t-PA in the resulting plasmids pSV-FGK1K2L and pSV-GK1L was examined by restriction analysis. FIG. 1 shows diagrammatically the production of the plasmid pSV-GK1L as well as the position of individual elements on the plasmid.

CHO dhfr$^-$cells (ECACC 88072103) were transformed with the recombinant vectors pSV-FGK1K2L and pSV-GK1L (Proc. Natl. Acad. Sci. USA 76 (1979), 4350-4354). For this calcium phosphate precipitates were prepared with 20 μg pSV-FGK1K2L or pSV-GK1L in a volume of 4 ml (Virology 52 (1973), 456-467). 1 ml of the precipitate was added to 3 ×10$^5$ to 1×10$^6$ cells in 10 ml medium. The cells were incubated for 8-16 hours, the medium was then removed, the cells washed with 10 ml TBS (25 mmol/l Tris-HCl, pH 7.4, 137 mmol/l NaCl, 5 mmol/l KCl, 0.6 mmol/l NaH$_2$PO$_4$) and then incubated in a suitable medium. 48 hours after transfection the CHO dhfr$^-$cells (ECACC 88072103) were diluted 1 : 10 and then cultured in a selection medium (J. Mol. Biol. 159 (1982), 601-621). The clones which formed were trypsinized 2 to 3 weeks after the transfection with the aid of a cloning cylinder, they were grown to a mass culture and the supernatants were examined by ELISA (Gene 51 (1987) 31-41) for t-PA immunoreactivity. Positive clones were incubated in a medium containing 20 nmol/l methotrexate. Methotrexate-resistant colonies appeared after 2 weeks. They were cultured to confluence and exposed to 100 nmol/l methotrexate in the medium. Resistant cells were exposed to methotrexate concentrations which were increased stepwise (300 nmol/l, 500 nmol/l, 1 μmol/l and 5 μmol/l). Clones were isolated by limit dilution and those which produced t-PA best were selected.

CHO cells which showed constitutive secretion of wild-type t-PA or GK1L were cultured in DMEM medium (Dulbecco's modified Eagle Medium) supplemented with 10% fetal calf serum in the presence and absence of aprotinin (50 μg/ml). The supernatants were adjusted with HCl to 0.3 mol/l arginine pH 7.5 and applied to an ETI sepharose column (J. Biol. Chem. 259 (1984) 11635-11638). The proteins were eluted with 20 mmol/l citrate buffer, pH 2.5 and subsequently dialysed against 20 mmol/l Tris HCl, pH 7.5.

Aliquots of the purified proteins to which 10 μg cytochrome C was added were precipitated for one hour with 4 volumes acetone at 20° C. and subsequently dissolved in Laemmli sample buffer. The protein samples were boiled for 3 minutes and separated on a 12.5% SDS polyacrylamide gel using a discontinuous buffer system (Laemmli, Nature 227 (1970), 680-685). After the electrophoresis the gels were electroblotted onto nitrocellulose filters. The filters were washed with TBS and then saturated at room temperature for 30 to 60 minutes with TBS +0.05% Tween +3% gelatin and finally briefly washed with water. Afterwards the membrane filters were treated for 1 hour at room temperature with a 1:1000 dilution of a peroxidase-conjugated goat antibody against human t-PA in TBS +0.5% bovine serum albumin. In order to visualize the immunocomplexes the filters, after a further threewashing steps with TBS, were incubated with a 1:1 solution of 2.5 mmol/l tetramethylbenzidine and 4.5 mmol/l sodium dioctylsulfosuccinate in methanol and 0.005% hydrogen peroxide in 0.1 mol/l citric acid buffer, pH 5. The Rainbow-Mix (Amersham) which contains the following proteins: myosin, 200 kd, phosphorylase 92.5 kd, bovine serum albumin, 69 kd, ovalbumin, 46 kd, carboanhydrase, 30 kd, trypsin inhibitor, 21.5 kd and lysozyme, 14 kd, was used as a marker for the polyacrylamide gel electrophoresis.

The culture supernatant of cells which contain the plasmid pSV-GK1L which expresses GK1L gives an immunoreactive band of about 50000 daltons (corresponding to the single-chain form of GK1L), a band of about 31000 daltons (corresponding to the L chain) and a band of about 19000 daltons (corresponding to the H chain) when treated with antibodies against t-PA. When the cell medium contains the protease inhibitor aprotinin the proportion of double-chain molecules decreases in comparison to the single-chain molecules.

In contrast t-PA has a band of 65000 to 68000 daltons (corresponding to the single-chain form) and 2 bands of 34000 or 31000 daltons (corresponding to the H or L chain).

EXAMPLE 3

Comparison of the fibrinogen-stimulated catalytic activities of t-PA and GK1L t-PA and GK1L were concentrated from the supernatants of CHO cells as described in Example 2. In this process the CHO cells which secrete t-PA or GK1L were cultured in the presence or absence of aprotinin (50 μg/ml). In order to carry out the activity test the supernatants were diluted 1:250 which resulted in a negligibly small inhibitor concentration. The plasminogen-cleaving activity was determined by an indirect spectrophotometric test (Thromb. Haemostasis 48 (1982), 266-269). t-PA converts plasminogen into the active serine protease plasmin which hydrolyses a bond of a chromogenic substrate whose absorbance was measured at 405 nm for a period of up to 3 hours. In modified experiments tosylated Gly-Pro-Lys-p-nitroanilide (Chromozy ® PL) was used as the chromogenic substrate. The tests were carried out at 25° C. in 0.1 mol/l TrisHCl, pH 7.5, 0.15 mol/l Tween 80 and 0.13 μmol/l plasminogen and 0.30 mmol/l Chromozy ® PL in the absence or presence of fibrinogen cleaved with CNBr (120 μg/ml). The absorbance was determined at 405 nm as a measure for the release of p-nitrophenol from the chromogenic substrate and recorded as a function of the incubation period. The results are shown in FIG. 2.

The plasminogen-cleaving activity of t-PA (isolated from supernatants free of aprotinin) is represented by filled-in circles, the activity of t-PA (isolated from supernatants containing aprotinin) is represented by open circles, the activity of GK1L (isolated from supernatants containing aprotinin) is represented by filled-in squares and the activity of GK1L (isolated from supernatants without aprotinin) is represented by open squares. ±CNBr shows the presence or absence of fibrinogen fragments treated with CNBr in the test. (+) or (−) shows whether the protein was purified from tissue culture supernatants containing aprotinin or free of aprotinin.

From FIG. 2 it can be seen that a stimulation of the catalytic activity of GK1L results in the presence of fibrinogen.

In this case it is surprising that the catalytic activity, with and without fibrinogen, of a supernatant of cells which express GK1L is significantly higher than that of a supernatant of cells expressing wild-type t-PA. If aprotinin is present in the medium the activity of GK1L is higher in the presence of fibrinogen and lower without fibrinogen than without aprotinin.

I claim:

1. Human tissue type plasminogen activator derivative having an amino acid sequence corresponding to amino acids 50-175 and 262-527 of FIG. 3.

2. Human tissue type plasminogen activator derivative of claim 1, wherein said derivative is glycosylated at its natural glycosylation sites.

3. Fibrinolytic agent comprising a human tissue type plasminogen activator of claim 1 and a carrier.

* * * * *